United States Patent [19]
Bonutti

[11] Patent Number: 5,167,612
[45] Date of Patent: Dec. 1, 1992

[54] ADJUSTABLE ORTHOSIS

[76] Inventor: Peter M. Bonutti, P.O. Box 1387, Watson, Ill. 62401

[21] Appl. No.: 559,700

[22] Filed: Jul. 30, 1990

[51] Int. Cl.[5] .............................................. A61F 5/10
[52] U.S. Cl. .................................. 602/20; 128/25 R; 602/5; 602/16
[58] Field of Search ............... 128/25 R, 26, 77, 80 C, 128/80 F, 88; 272/117–119, 139, 140, 143, 126; 602/5, 16, 20, 23, 26

[56] References Cited

U.S. PATENT DOCUMENTS

| | | |
|---|---|---|
| 3,814,419 | 6/1974 | Bjorklund et al. |
| 4,039,183 | 8/1977 | Sakurada |
| 4,180,870 | 1/1980 | Radulovic et al. |
| 4,237,873 | 12/1980 | Terry et al. |
| 4,441,489 | 4/1984 | Evans et al. |
| 4,456,002 | 6/1984 | Barber et al. |
| 4,508,111 | 4/1985 | Hepburn |
| 4,538,600 | 9/1985 | Hepburn |
| 4,612,919 | 9/1986 | Best |
| 4,665,905 | 5/1987 | Brown |
| 4,790,301 | 12/1988 | Silfverskiold |
| 4,844,454 | 7/1989 | Rogers |
| 4,848,326 | 7/1989 | Lonardo |
| 4,865,024 | 9/1989 | Hensley et al. ............ 602/26 X |
| 4,930,497 | 6/1990 | Saringer ................. 128/25 R |

FOREIGN PATENT DOCUMENTS 2829562 1/1980 Fed. Rep. of Germany.
1426580 9/1988 U.S.S.R.

Primary Examiner—Robert Bahr
Assistant Examiner—Linda C. M. Dvorak
Attorney, Agent, or Firm—Tarolli, Sundheim & Covell

[57] ABSTRACT

An adjustable orthosis for stretching tissue by moving a joint between first and second relatively pivotable body portions includes a first arm with a cuff at its outer end for releasably attaching the first arm to the first body portion, and a second arm with a cuff at its outer end for releasably attaching the second arm to the second body portion. The arms are pivotally connected at their inner ends. An actuator is connected to the arms for applying force to the arms to pivot them relative to each other to move the joint. The actuator includes flexible force transmitting means connected with at least one of the arms, and drive means for applying force to the flexible force transmitting means to move the first and second arms relative to each other. In a preferred embodiment, the flexible force transmitting means is a rope or cable and the drive means is a manually actuatable winch for winding the rope or cable. The drive means is located at a distance from the pivotal connection of the first and second arms. The orthosis is adjustable while on the limb to a plurality of different positions including at least a first position in which the joint is flexed to a relatively greater degree and a second position in which the joint is extended to a relatively greater degree. The orthosis can also be used to flex.

37 Claims, 8 Drawing Sheets

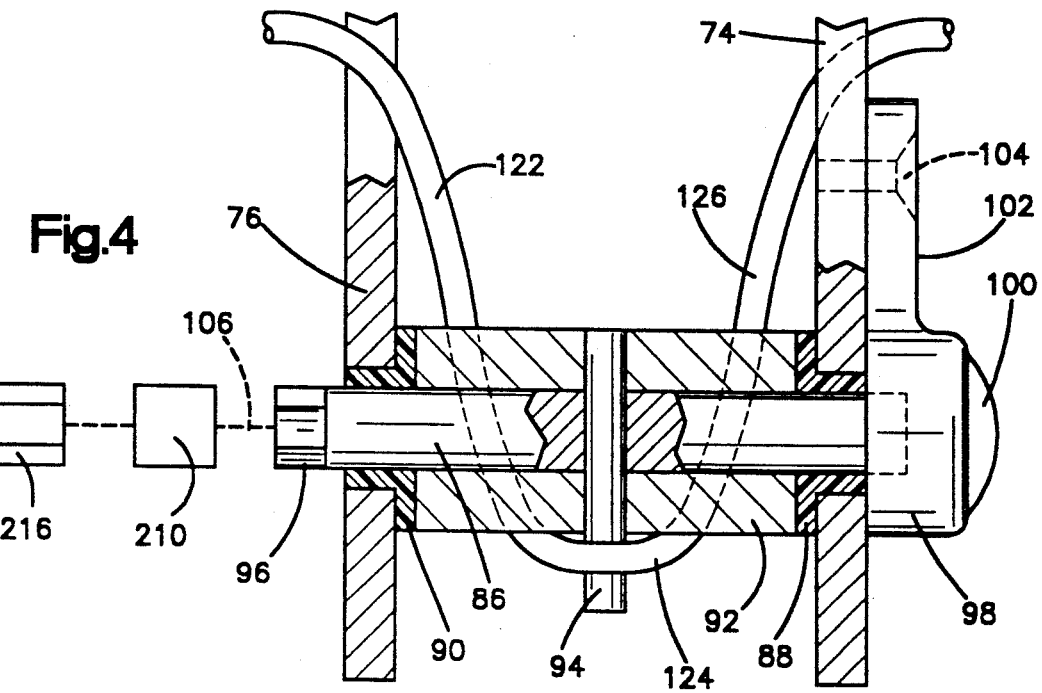
Fig.4
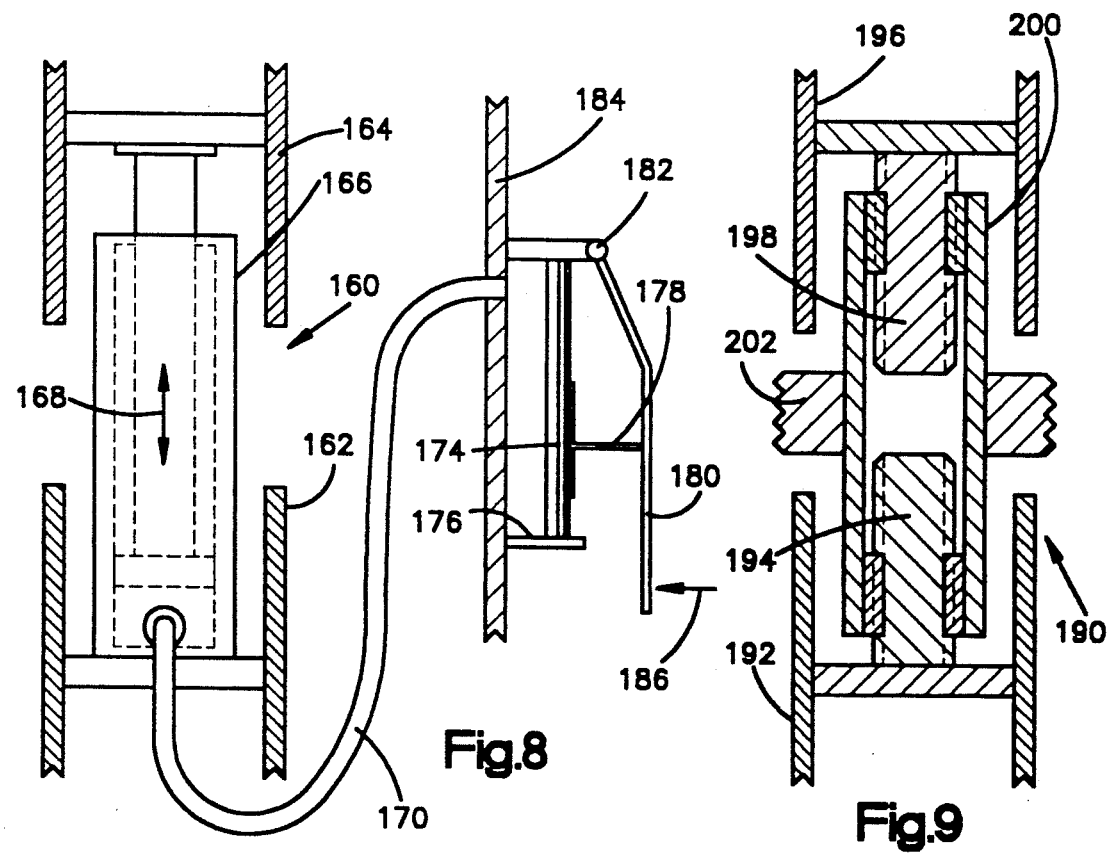
Fig.8
Fig.9

ADJUSTABLE ORTHOSIS

BACKGROUND OF THE INVENTION

1. Technical Field

The present invention relates to an adjustable orthosis for stretching tissue in the human body. In particular, the present invention relates to an adjustable orthosis which can be used for stretching tissue such as ligaments, tendons or muscles around any joint during flexion or extension of the joint.

2. Description of the Prior Art

Best U.S. Pat. No. 4,612,919 shows an adjustable limb support for adjustably orienting the forearm and upper arm of a human patient in a variety of angular relationships to therapeutically treat the contracted muscles in the patient's arm.

Lonardo U.S. Pat. No. 4,848,326 shows a knee contracture correction device for straightening a contracted knee. The device includes a pair of rod assemblies each having opposite upper and lower ends and a pivotal joint between the ends. The upper end of the rod assemblies is pivotally secured to the patient's thigh while the lower end is pivotally secured adjacent the patient's ankle. The pivotal joint of the rod assemblies is locked so as to define an obtuse angle slightly greater than the angle of contracture of the knee. Straps are then positioned immediately above and below the knee and fastened to the rod assemblies so as to stretch the knee ligaments and muscles. Periodically, the angle of the rod assemblies is increased until eventually the knee contracture is eliminated.

Hepburn U.S. Pat. No. 4,538,600 shows an adjustable splint assembly with a lower strut and an upper strut pivotably connected to the lower strut. An internal spring applies a force at the pivot point to align the upper and lower struts to straighten the limb to which the splint is attached. A similar device is also shown in Hepburn U.S. Pat. No. 4,508,111. Similar devices are in use and are sold under the trademark DYNASPLINT by Dynasplint Systems, Inc.

Rogers U.S. Pat. No. 4,844,454 shows a portable, manually operable knee exerciser having a handle grasped by the user to pivot the lower leg relative to the upper leg.

Brown U.S. Pat. No. 4,665,905 shows a dynamic elbow and knee extension device with a centrally positioned compression spring.

It is also known in the art to put a rigid element including a turnbuckle, on the inside angle of a joint, between two cuffs attached to limb segments and use the turnbuckle to vary the length of the rigid element to pull and push the limb segments relative to each other. It has been found that this device does not work very well in practice because it is cumbersome and difficult to obtain relatively full extension at the extreme of motion.

SUMMARY OF THE INVENTION

The present invention is an adjustable orthosis for moving a joint between first and second relatively pivotable body portions. The joint and the first and second body portions define on one side of the joint an inner sector which decreases in angle as the joint is flexed (bent) and on the opposite side of the joint an outer sector which decreases in angle as the joint is extended (straightened). The orthosis includes a first arm, first cuff means on the first arm for releasably attaching the first arm to the first body portion, a second arm, and second cuff means on the second arm for releasably attaching the second arm to the second body portion. The first and second arms are pivotally connected with each other intermediate the first and second cuff means. An actuator means is connected to the first and second arms for applying force to the first and second arms to pivot the first and second arms relative to each other to move the joint. The actuator means includes flexible force transmitting means connected with at least one of the arms, and drive means for applying force to the flexible force transmitting means to move the first and second arms relative to each other. The drive means is preferably supported in the outer sector at a distance from the pivotal connection of the arms substantial enough to ensure a significant mechanical advantage.

Tissue is viscoelastic. It will stretch, then return to (or almost to) its original state, but will have acquired a greater range of motion by having been stretched. Tissue requires intermittent forceful stretching to improve the range of motion. The key to good stretching is therefore graduated, progressive stressing (stretching) of the tissues at the joint. One avoids tissue damage by such gradual progressive modulated stretching of the tissue (stress relaxation of tissue). Gradual stretching does not damage tissues, as a sudden force would.

In therapy, one must first develop a range of motion before strengthening the muscles. The most difficult area is to work on the extremes of motion. A patient can't feasibly go to a therapist three times a day. The present invention provides an orthosis which a patient can use at home, by himself, without a therapist. The orthosis can be used up to several times a day so as not to lose, by long periods of inaction, the benefits gained from each stretching session. Since the patient is awake, he can modulate the force applied, preventing damage by stopping when it is too painful.

With the frequent use of this device, the tissues will progressively stretch out, for an improved range of motion. The patient can tighten the tissues, wait a few minutes, then tighten some more, progressively, using the stress relaxation ability of tissue. This also is practically not feasible with a therapist.

The flexible force transmitting means is preferably a rope or cable. Although a winch and rope are disclosed herein as the preferred drive means, any structure which controllably and progressively tightens a rope or cable or chain etc. can be used, not just a winch. The winch is the simplest, and has a releasable ratchet drive which prevents the orthosis from returning to a previous position after it is tightened to a certain degree.

The orthosis of the present invention also has a fine range of control with the winch for tension adjustment. The winch provides easily controllable and repeatable, graduated force.

It is desirable to stretch tissue without increasing the joint reactive force. Pulling apart a joint is mechanically advantageous to pushing it apart. There is less joint reactive force with the structure of the present invention. The greatest force is at the apex of the force triangle. With the tower design of the present invention, only a distractive force is applied to the tissue around the joint, and the apex of the distraction force is distant from the joint, so there is less force at the joint, and therefore less damage to the joint tissues. Thus, less compressive force is required to be placed on the joint to obtain the same results. The orthosis stretches the tissue around the joint without compressing the joint itself, which is the conjunction of two or more bones.

BRIEF DESCRIPTION OF THE DRAWINGS

Further features of the present invention will become apparent to those skilled in the art to which the present invention relates from reading the following specification with reference to the accompanying drawings, in which:

FIG. 4 is an enlarged view partially in section of the winch mechanism of the orthosis of FIG. 1;

FIG. 8 is an enlarged view of an adjustable length support member for an adjustable orthosis in accordance with a third embodiment of the present invention;

FIG. 9 is an enlarged view of a portion of an orthosis with another adjustable length support member.

DESCRIPTION OF PREFERRED EMBODIMENTS

The term "orthosis" is typically used to refer to a brace or other device applied to a portion of the body to correct malalignment of joints. The present invention is an adjustable orthosis for stretching tissue in the human body. In particular, the present invention relates to an adjustable orthosis which can be used for stretching tissue in a body. In the description below, the invention is described as embodied in an orthosis for stretching tissue around a joint, although the invention is not limited thereto.

Figure 1:
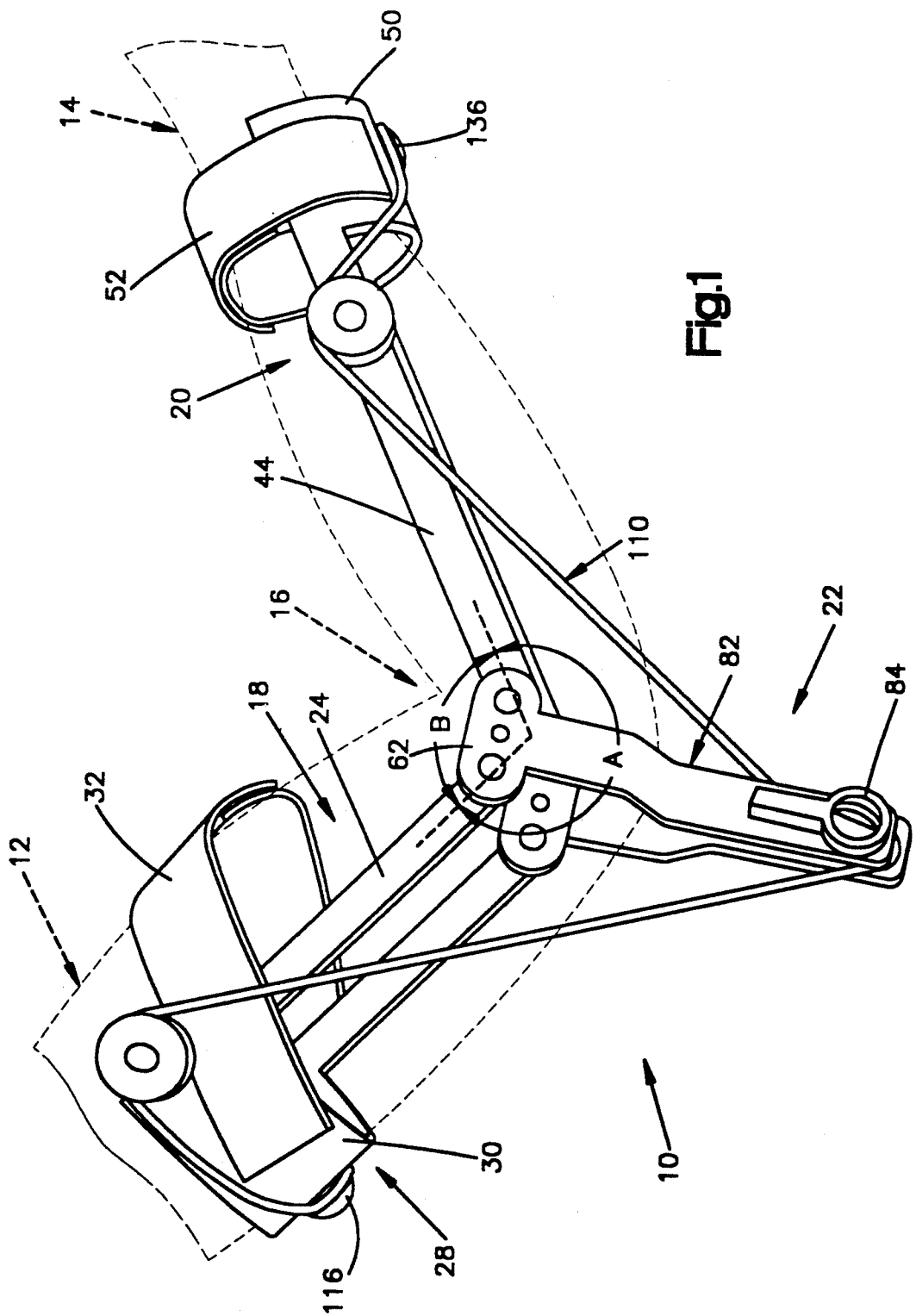
FIG. 1 is a perspective view of an adjustable orthosis embodying the present invention shown in a flexed position on an arm of a patient and set up to extend an elbow joint.

FIG. 1 illustrates an orthosis 10 in accordance with the present invention on a human limb including an upper arm 12 and a forearm 14 pivotally connected at an elbow joint 16. The orthosis 10 is illustrated as set up to extend (straighten) the elbow joint 16, although it should be understood that the orthosis 10 can also be set up to flex (bend) the elbow joint 16, as will be described later. It should also be understood that the orthosis 10 can be used to extend or flex other joints in the body, such as a knee joint or a wrist joint or ankle joint, with the construction of the orthosis 10 in such case being varied to fit the particular application. The orthosis can be used, for example, to flex the ankle joint to stretch a tight achilles tendon. It is especially useful in obtaining the last degrees of joint extension. The orthosis can be custom made to fit a particular individual, or can be an off the shelf item. The orthosis can also be used, for example, to eliminate contractures or stress soft tissue. It can be used for patients with cerebral palsy, stroke, spastic paralysis, as well as in post-traumatic or post-surgical cases. It can also be used, for example, in therapy after a knee replacement, in which the last five to ten degrees of motion is difficult to obtain without extensive intervention of a therapist.

The orthosis 10 includes a first arm assembly 18, a second arm assembly 20, and an actuator assembly 22 operable to pivot the first arm assembly 18 relative to the second arm assembly 20 to move the joint 16. (As used herein, the term "move a joint" means either to extend the joint or to flex the joint.)

Figure 2:
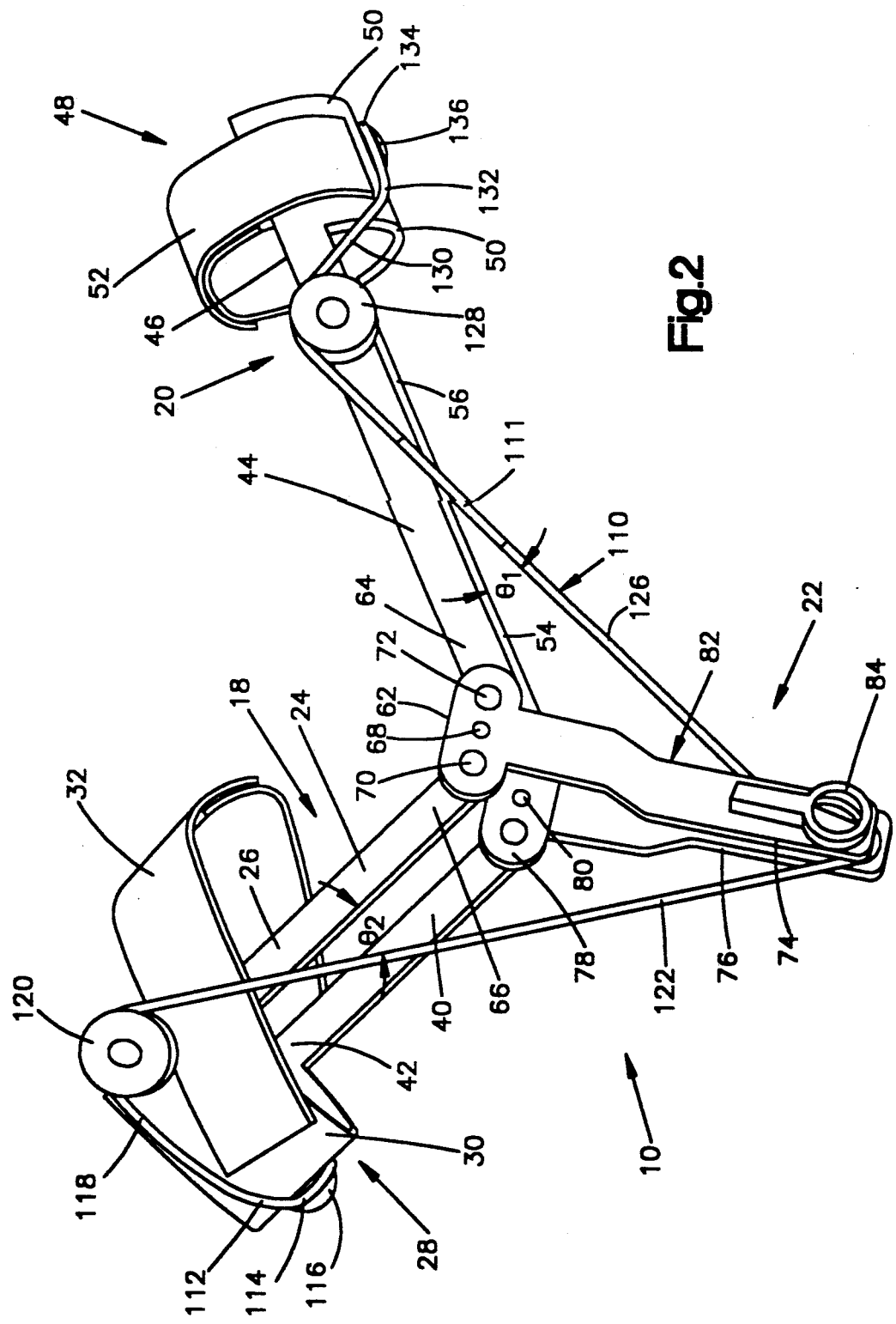
FIG. 2 is a view of the orthosis of FIG. 1 removed from the arm of the patient.

The first arm assembly 18 includes a rigid longitudinally extending arm 24 (FIGS. 1 and 2). To the outer end portion 26 of the arm 24 is attached a first cuff assembly 28. The first cuff assembly 28 includes a rigid cuff portion 30 and a flexible cuff portion 32. The rigid cuff portion 30 extends approximately halfway circumferentially about the upper arm 12, and the flexible cuff portion 32 wraps about the remainder of the upper arm 12. Suitable fastening means such as Velcro ® is used to secure the first cuff assembly 28 to the upper arm 12 so that the first arm assembly 18 may apply torque to the upper arm 12.

The first arm assembly 18 also includes a rigid longitudinally extending arm 40, which is shown in FIG. 2 but not in FIG. 1 as it is behind the upper arm 12. An outer end portion 42 of the arm 40 is also attached to the rigid cuff portion 30 of the first cuff assembly 28. The arm 40 extends parallel to the arm 24 and is spaced apart from the arm 24, with the arms 24 and 40 on opposite sides of the upper arm 12 of the limb.

The second arm assembly 20 includes a rigid longitudinally extending arm 44. To an outer end portion 46 of the arm 44 is attached a second cuff assembly 48. The second cuff assembly includes a rigid cuff portion 50 and a flexible cuff portion 52 attached thereto. The rigid cuff portion 50 extends approximately halfway about the forearm 14, and the flexible cuff portion 52 wraps about the remainder of the forearm 14. Suitable fastening means such as Velcro ® is used to secure the second cuff assembly 48 about the forearm 14, so that the second arm assembly 20 can apply torque to the forearm 14.

The second arm assembly 20 also includes a rigid longitudinally extending arm 54 which is shown in FIG. 2 but not in FIG. 1. This arm 54 extends parallel to and spaced apart from the arm 44, with the arms 54 and 44 on opposite sides of the forearm 14. An outer end portion 56 of the arm 54 is attached to the rigid cuff portion 50.

The actuator assembly 22 includes a tower 82 which is provided to move the force generating point (that is, the point from which force is directed to the arm assemblies) away from the axis of rotation of the joint to obtain a mechanical advantage. The tower can be any structure which preforms this structure, and need not be the structure shown herein. The tower 82 has a tower connecting portion 62 to which the inner end portions 64 and 66 of the arms 44 and 24 respectively are connected. On the back of the arms 44 and 24 as viewed in FIG. 2 is a pivot plate (not shown) which is fixed by a rivet 68 to the tower connecting portion 62. The tower connecting portion 62 and the pivot plate secure the arm 24 for pivotal movement about a pivot point 70, and the arm 44 for pivotal movement about a pivot 72. Similarly, the tower includes a second tower portion 76 which joins the arms 40 and 54. An inner pivot plate 78 is fixed via a rivet 80 to the second tower portion 76 and provides for pivotal movement of the arms 40 and 54 relative to each other.

Together, the first tower portion 74 and the second tower portion 76, which form the tower 82, support a winch 84 at a substantial distance from the pivot points 70 and 72 of the arms 24 and 44, and at a substantial distance from the pivot points of the arms 40 and 54. (By "substantial" is meant far enough to provide a mechanical advantage as compared to orthoses which apply force at a location adjacent the axis of rotation of the joint. The benefit of this is discussed later herein.) The upper arm 12, elbow joint 16, and forearm 14 define on one side of the joint 16 an inner sector "B" (inside the bend of the limb) which decreases in angle as the joint 16 is flexed. The upper arm 12, the elbow joint 16, and the forearm 14 define on the opposite side of the joint 16 an outer sector "A" which decreases in angle as the joint 16 is extended (straightened). The tower 82 and the winch 84 are located in the outer sector "A".

The winch 84 includes a drive member 86 (FIG. 4) which extends between the tower portion 76 and the tower portion 74. One end of the drive member 86 is received in a bearing 88 in an opening in the tower portion 76, and the opposite end of the drive member 86 is received in a bearing 90 in a corresponding opening in the tower portion 74. A drum 92 is fixed by a pin 94 to the drive member 86. Wrenching flats 96 are formed on one end of the drive member 86. The opposite end of the drive member 86 is received in a ratchet drive 98 which includes a pawl trigger 100. A leg portion 102 of the ratchet drive 98 is fixed via a suitable fastener such as a screw 104 to the tower portion 76.

A flexible member 110 (FIG. 2) is included in the actuator assembly 22. In the preferred embodiments, the flexible member 110 is a rope. A first end portion 112 of the rope 110 terminates in clip 114 which is fixed via a pin 116 to the rigid cuff portion 30 of the first arm assembly 18. A portion 118 of the rope 110 wraps around a pulley 120. A portion 122 of the rope extends from the pulley 120 to the winch 84. The rope 110 then wraps around the pin 94 (FIG. 4) as at 124 and a portion 126 of the rope 110 extends thence to a pulley 128 on the second arm assembly 20. A portion 130 of the rope wraps around the pulley 128. The other end portion 132 of the rope 110 terminates in a clip 134 fixed by a pin 136 to the rigid cuff portion 50 of the second cuff assembly 48. Thus, both ends of the rope 110 are fixed to the cuff assemblies, while the middle portion of the rope 110 is windable by the winch 84.

The orthosis 10 is operated to extend a joint such as the joint 16 in the following manner. The first cuff assembly 28 is fastened about the upper arm 12 tightly enough that the first arm assembly 18 may apply torque to the upper arm 12 without having the cuff assembly 28 slide along the upper arm 12. Similarly, the second cuff assembly 48 is fastened securely around the forearm 14 so that the second arm assembly 20 may apply torque to the forearm 14 without the cuff assembly 48 sliding along the forearm 14. The drive member 86 of the winch 84 is then rotated about its axis 106 to wind the rope 110. The rope portions 122 and 126 are partially wound onto the drum 92. Because the rope end 112 is fixed to the first cuff assembly 28, and the other rope end 132 is fixed to the second cuff assembly 48, the cuff assemblies 28 and 48 are drawn toward the winch 84. The first arm assembly 18 pivots about the pivot point 70, and the second arm assembly 20 pivots about the pivot point 72. As the arm assemblies 18 and 20 pivot, the upper arm 12 and forearm 14, to which they are attached, also pivot. This moves or extends the joint 16 as was desired.

Figure 3:
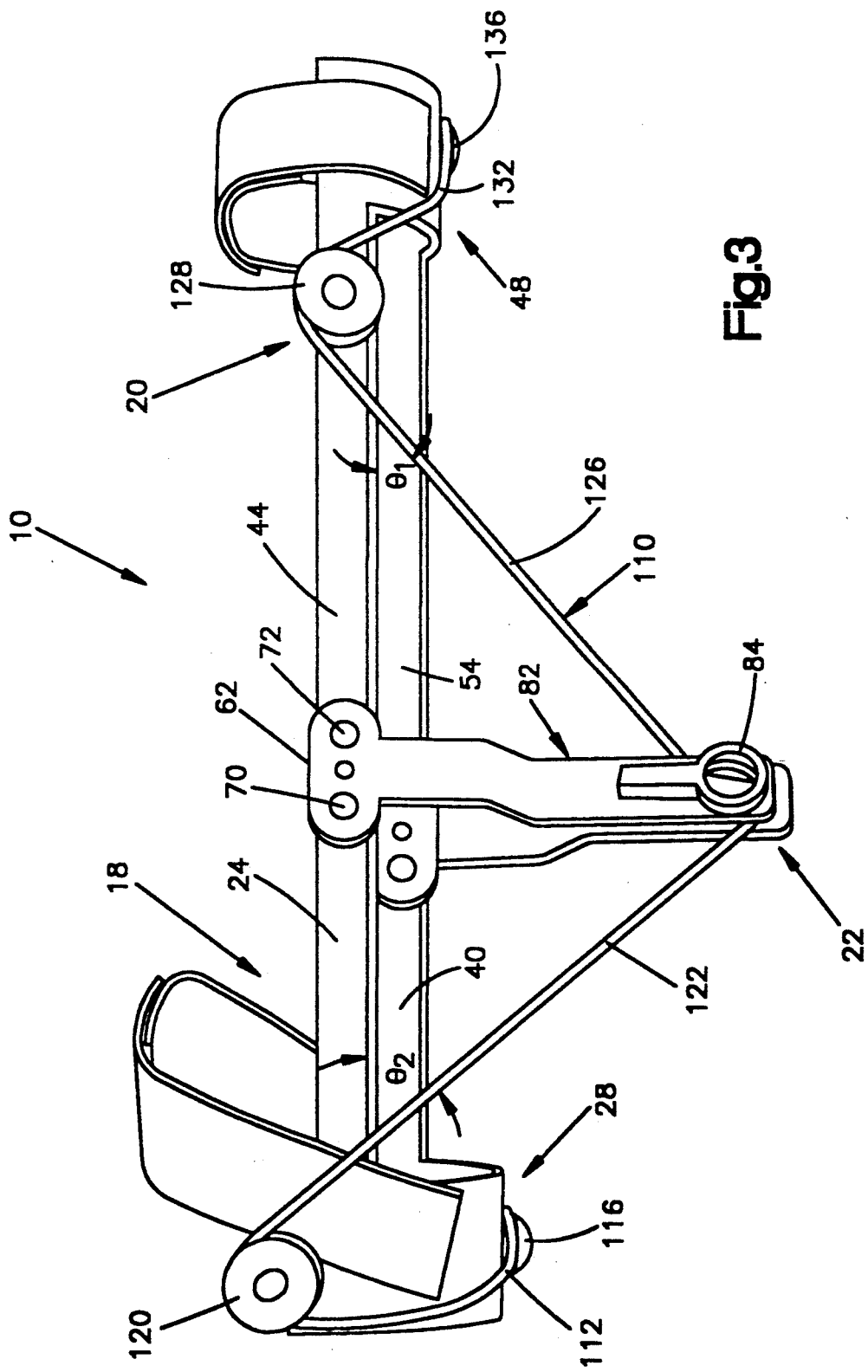
FIG. 3 is a view of the orthosis of FIG. 1 in an extended position.

As the orthosis 10 is adjusted to extend the joint 16 from the relatively flexed position shown in FIG. 2 to the relatively extended position shown in FIG. 3, the acute angle $\Theta_2$ (FIG. 2) between the rope portion 122 and the first arm assembly 18 increases. At the same time, the acute angle $\Theta_1$ (FIG. 2) between the rope portion 126 and the second arm assembly 20 also increases as the orthosis i adjusted from the relatively flexed position shown in FIG. 2 to the relatively extended position shown in FIG. 3.

The torque applied by a cuff assembly to its respective limb portion is equal to (1) the force applied along the rope portion extending from the winch 84 to that arm assembly, times (2) the length of the lever arm of that arm assembly, times (3) the sine of the angle between the rope portion and the arm assembly. For example, referring to FIG. 2, the torque applied to the first arm assembly 18 at the pulley 120 is equal to the force applied along the rope portion 122, times the lever arm (which is equal to the distance between the pivot 70 and the pulley 120), times the sine of the angle $\Theta_1$ between the rope portion 122 and the arm 24 or the arm 40.

As the orthosis 10 is adjusted from a relatively flexed position as viewed in FIG. 2 to a relatively extended position as viewed in FIG. 3, the angle between a rope portion (122 or 126) and its respective arm assembly (18 or 20) increases. Thus, the sine of the angle between the rope portion and the arm assembly also increases. For any given orthosis, the length of the lever arm is a constant. Thus, assuming a constant force applied by the winch 84 pulling on the rope portion 122, a greater amount of torque is applied by the arm assembly to the limb portion as the orthosis 10 is adjusted from a relatively flexed position as viewed in FIG. 2 to a relatively extended position as viewed in FIG. 3.

Since terminal stretching, that is, extension through the last degrees of a range of motion, is the most difficult in a human joint, the orthosis of the present invention is highly advantageous in that the amount of torque available to pivot the upper arm relative to the forearm increases as the joint is extended. The orthosis provides a large straightening force through the full range of motion because it maintains a significant vertical (extension) force vector through the full range of motion. Of course, this assumes a sufficient force applied to and by the winch 84, and it is understood that more force may be needed to turn the winch 84 as the joint is fully extended to overcome the stiffness of the joint.

The force vector representative of the pulling force extending along the flexible member 110 can be resolved into a component extending in a direction parallel to the arm assembly and a component extending in a direction perpendicular to the arm assembly. The force component extending in the direction perpendicular to the arm assembly is representative of the magnitude of the net extension force applied to the arm assembly to extend the joint. This component is equal to the sine of the angle between the flexible member and the arm assembly, times the force in the direction along the flexible member.

The net extension force is therefore directly proportional to the sine of the angle between the flexible member and the arm assembly. Thus, to increase the extension force applied to the arm assembly, the angle can be increased. It can be seen that one way to increase the angle is to increase the distance between the pivot point for the arm assembly and the drive means. Thus, it is evident that the longer the support member or tower, the greater the extension force.

Thus, the structure of the orthosis 10 is clearly advantageous as compared to, for example, a prior art device which applies its force at a location closely adjacent to the joint. For such a device, the distance between the force application point and the pivot point of the arm is very short. Thus, the angle between (a) the arm and (b) a line extending between the cuff assembly and the force generation point, is always extremely small. Accordingly, the amount of torque which can be generated is extremely limited. Thus, having the winch or drive means 84 spaced at a substantial distance from the pivot points 70 and 72 by the tower 82, as in the illustrated embodiments, provides a substantial mechanical advantage.

It can also be seen that, when the winch 84 pulls on the flexible member 110, a reaction force is developed in the rigid tower or support member 82. The reaction force extends along the tower 82 in the direction from the winch 84 to the pivots 70 and 72 and the to pivots for the arms 40 and 54. The reaction force 84 tends to push in one direction on the inner end portions of the arms 24, 40, 44, and 54, while the pulling force generated by the winch 84 moves the outer end portions of the same arms in the opposite directions. Thus, the actuator assembly 22 simultaneously applies oppositely directed forces to opposite ends of the arm assemblies 18 and 20 to provide an even more efficient pivoting motion to extend the joint 16.

It should be noted that the pulley 120 is in a different position on the first arm assembly 18 than the pulley 128 is on the second arm assembly 20. The location of the pulleys is a matter of design choice. As a pulley is moved farther out along its arm assembly from the pivot point, the lever arm and thus the torque applied to the arm assembly by the winch 84 pulling on the flexible member 110 increases. The pulley is also preferably located as far from the rope end portions as possible in a direction transverse to the longitudinal extent of the arms. For example, the pulley 120 is farther from the pin 116 in a direction transverse to the arm 24, than the pulley 128 is from the pinion 136 in a direction transverse to the arm 44. Moving the pulley farther away in this manner increases the angle between the rope portions and the arm assemblies, thus increasing the available torque.

It should also be noted that the orthoses of the present invention are suitable to hyperextend a joint, also. Preferably, the orthosis is constructed so that the joint when fully extended is hyperextended by 5° to 7°. This provides the fullest range of motion desired. This can be accomplished by construction of the pivotal connection between the arm assemblies to allow for such hyperextension.

Figure 5:
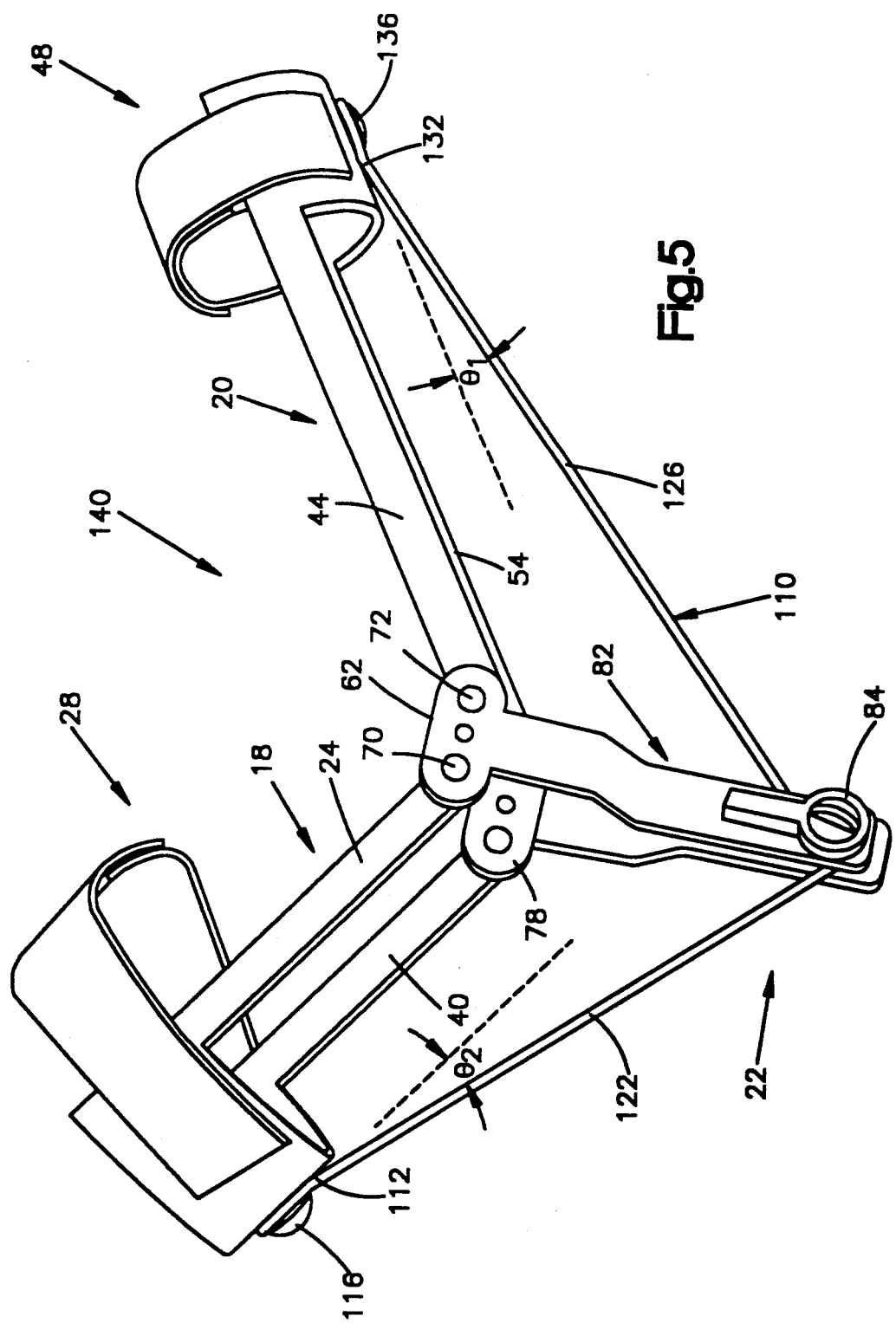
FIG. 5 is a perspective view of an adjustable orthosis in accordance with a second embodiment of the present invention and shown in a flexed position.
Figure 6:
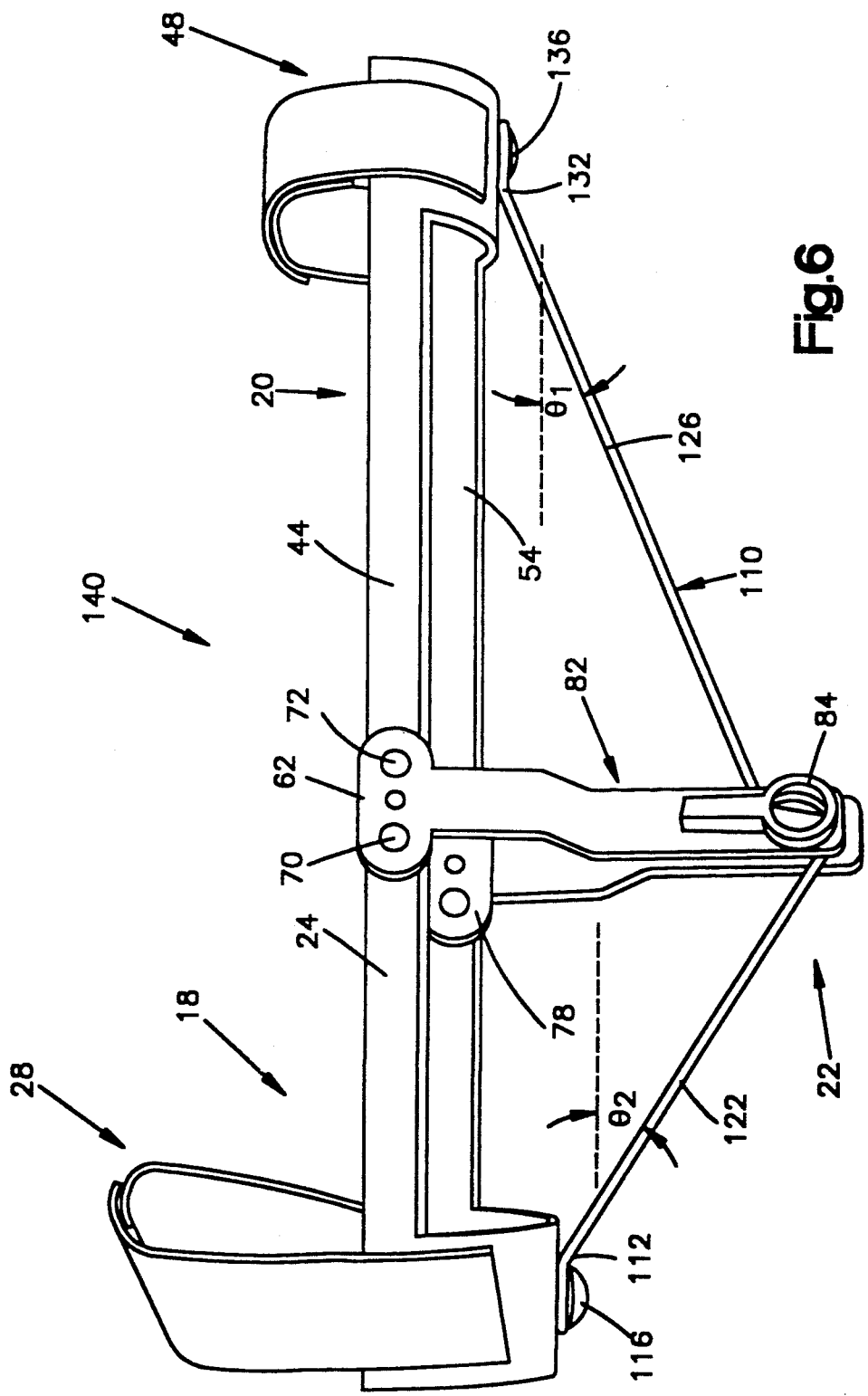
FIG. 6 is a view of the orthosis of FIG. 5 in an extended position.

A second embodiment of the invention is illustrated in FIGS. 5 and 6, in which parts which are the same as in the first embodiment are given the same reference numerals. An orthosis 140 includes a flexible member 110 which does not extend around pulleys but extends directly from the winch 84 to the cuff assemblies 28 and 48. The orthosis 140 is, like the orthosis 110, adjustable between a relatively flexed position as viewed in FIG. 5 and a relatively extended position as viewed in FIG. 6. Manual actuation of the winch 84 draws or pulls the rope portions 122 and 126 to wind them on the winch 84, shortening the distance between the cuff assemblies 28 and 48 and the winch 84. Because the inner ends of the arms 24, 40, 44, and 54 are pivotally mounted to the tower 82, the arm assemblies 18 and 20 pivot relative to each other to move the joint 16 into a more extended position.

With the orthosis 140, again, the acute angle $\Theta_1$ between the rope portion 126 and the second arm assembly 120, and the acute angle $\Theta_2$ between the rope portion 122 and the first arm assembly 18, increase in degree as the orthosis 140 is adjusted from the more flexed position shown in FIG. 5 to the more extended position shown in FIG. 6. Furthermore, placement of the winch or drive means 84 at substantial distance from the pivot points 70 and 72, as in the embodiment illustrated in FIGS. 5 and 6, ensures that a significant mechanical advantage is obtained.

Figure 7:
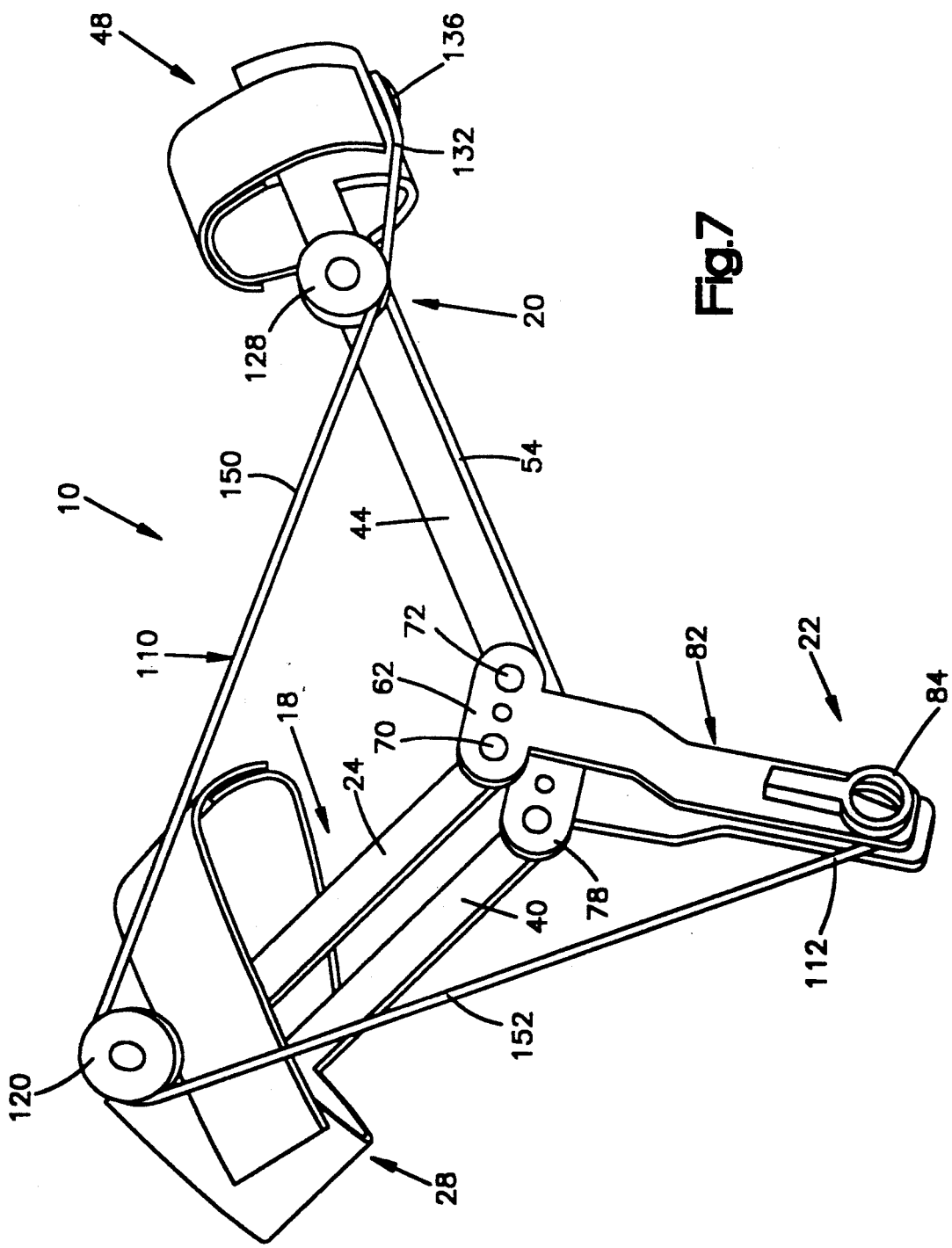
FIG. 7 is a view of the orthosis of FIG. 1 set up to flex a joint.

The orthosis 10 is illustrated in FIGS. 1 through 4 as being used to extend a joint. The orthosis 10 can also be used to flex a joint as illustrated in FIG. 7. This is done by rerouting the flexible member 110. The end portion 132 (FIG. 7) of the flexible member 110 remains fixed by the pin 136 to the second cuff assembly 48. A portion 150 of the rope 110 then extends underneath the pulley 128 over to the pulley 120. The rope 110 then extends around the pulley 120 and a portion 152 of the rope 110 extends to the winch 84. The end portion 112 of the rope 110 is tied or otherwise fixed to the winch 84.

When the winch 84 is then manually operated, the rope 110 will be wound to the drum of the winch 84. The second cuff assembly 48 will be drawn toward the first cuff assembly 28. Because the inner ends of the arm assemblies 18 and 20 are fixed to the tower 82 the arm assemblies 18 and 20 pivot relative to each other, decreasing the included angle between them. Since the arm assemblies 18 and 20 are fixed to the limb portions 12 and 14, the joint 16 is flexed.

As noted above, the net extension force is therefore directly proportional to the sine of the angle between the flexible member and the arm assembly. One way to increase the angle is to increase the distance between the pivot point for the arm assembly and the drive means. Accordingly, in a third embodiment of the invention, the actuator assembly for pivoting the first and second arm assemblies 18 and 20 includes, in place of the tower 82 and the winch 84, a variable length tower with a pulley at its outer end. Extending the variable length tower to move the pulley farther away from the pivot points of the arm assemblies 18 and 20, causes the arm assemblies 18 and 20 to pivot relative to each other to flex the joint 16.

The variable length feature of the tower assembly can be obtained in many different ways. FIGS. 8 and 9 illustrate two ways of constructing the variable length tower assembly.

In FIG. 8, a tower assembly 160 includes a fixed portion 162 (only a part of which is shown) upon which the arm assemblies 18 and 20 (not shown) are pivoted. A tower portion 164 is movable axially relative to the fixed tower portion 162. A pneumatic ram assembly 166 is actuatable in an axial direction as indicated by arrow 168 upon the introduction of fluid under pressure through a fluid supply line 170. A pulley (not shown) is mounted for rotation on the outward end of the movable tower portion 164. A flexible member or rope 110 (not shown) passes over the pulley and is not fixed to the pulley 172. Upon the introduction of fluid under pressure through the fluid supply line 170, the pneumatic ram assembly 166 causes the movable tower portion 164 to move outwardly relative to the fixed tower portion 162. Such motion causes the pulley to move away from the pivot points for the arm assemblies 18 and 20. This exerts a pulling force on the flexible member which extends around the pulley. This pulling force, as above, causes the arm assemblies 18 and 20 to pivot relative to each other to extend the joint 16 to which the orthosis is attached.

Fluid under pressure may be supplied to the supply line 170 in any known manner. One specific apparatus, which is operable by hand and thus usable by the patient, is illustrated in FIG. 8 and includes a piston 174 disposed within a chamber 176. An arm 178 connects the piston 174 to a handle 180 which is pivotally mounted at 182 to a base 184. When the handle 180 is moved (squeezed) toward the base 184 in the direction indicated by arrow 186, the piston 174 forces air through the fluid supply line to supply the pneumatic ram assembly 166. It should be understood that any means of supply fluid under pressure could suitably also be used.

Another manner of construction for an extendible tower assembly is indicated schematically in FIG. 9. The tower assembly 190 includes a fixed tower portion 192 having a threaded member 194 projecting outwardly therefrom, and a movable tower portion 196 having a threaded member 198 projecting inwardly therefrom. A sleeve nut 200 threadedly engages the threaded members 194 and 198 and has a handle portion or thumbwheel 202 extending radially therefrom. A pulley (not shown) is mounted on the movable tower portion 196 as in the construction illustrated in FIG. 8. Similarly, the fixed tower portion 192 is connected to the first and second arm assemblies. When the handle portion 202 is manually rotated about the longitudinal axis of the extendible tower 190, the movable tower portion 196 moves axially relative to the fixed tower portion 192. Accordingly, axial movement of the movable tower portion 196 away from the fixed tower portion 192 produces a pulling force on the rope 110, causing the first and second arm assemblies 18 and 20 to pivot relative to each other, thus extending the joint 16.

Figure 10:
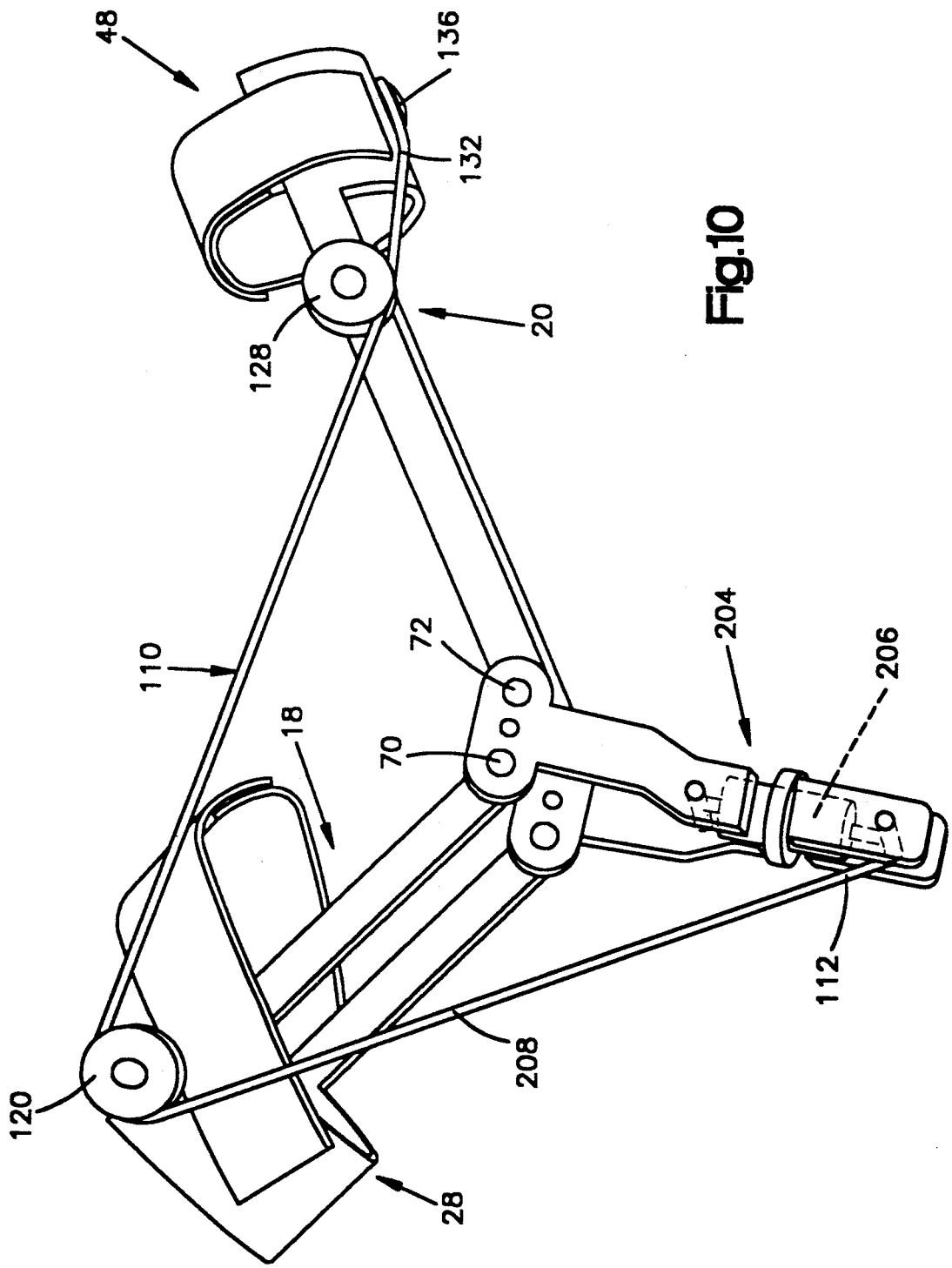
FIG. 10 is a view of the orthosis of FIG. 9 set up to flex a joint.

An extendible tower assembly can also be used in an orthosis set up to flex a joint rather than an extended joint. FIG. 10 illustrates such a construction. The one end portion 132 of the rope 110 is fixed to one cuff assembly 40. However, the opposite end portion 112 of the rope 110 is fixed to an outer end 206 of the extendible tower 204. When the extendible tower assembly 204 of the orthosis shown in FIG. 10 is made longer, increasing the distance between the pulley 206 and the pivotal connection with the arm assemblies 18 and 20, a pulling force is generated on the rope portion 208, drawing the cuff assemblies 28 and 40 closer to each other. This causes the arm assemblies 18 and 20 to pivot relative to each other to decrease the angle between them, thus flexing a joint to which the orthosis is attached. Thus, it can be seen that the extendible tower assembly is usable in both flexion and extension modes, just as the tower with a winch or other type of drive means is usable in both flexion and extension modes.

It should be noted that other configurations of the illustrated orthoses are possible when the orthoses are set up for flexion. The flexible member 110 can be routed in other ways to achieve flexion. Similarly, extension can be achieved by the illustrated orthoses when the flexible member 110 is routed differently, by moving pulleys or attachment points. Such variations on the illustrated embodiments, within the ordinary skill of the art, are part of the present invention and are covered by the appended claims.

In a further improvement, the illustrated orthoses may also include means for monitoring the amount of force transmitted through the flexible member 110 to the arm assemblies 18 and 20. Further, the orthoses may include relief means for limiting the amount of force transmitted to the arms 18 and 10. Such means are indicated schematically at 210 in FIG. 4 as being in the line of force transmission between the drive member 86 and an extension 216 thereof. The force monitoring or limiting means can be something as simple as a torque wrench applied to the drive member 86, or it can be a more complex mechanical structure, or it can be electronically controlled or operated. Thus, the box 210 illustrates schematically the provision or placement of force measuring and/or limiting means within the force path between the point at which the actuator is manually actuated and the cuff assemblies which transmit force to the arm portion. Such means can also be included, for example, within the flexible member itself, or at the pivot points, or at any other suitable location. Provision of such force monitoring or limiting means is within the skill of the art and thus is not described further herein.

The arms 24, 40, 44, and 54 are rigid members made of, for example, aluminum or stainless steel. The arms are rigid so as to be able to transmit the necessary forces. Similarly, the tower 82 and any extensible tower is also made of suitable material such as aluminum or stainless steel in order to provide a rigid structure capable of transmitting the necessary forces. It should be understood that any material of sufficient rigidity can be used, including a polymeric or composite material.

It should be understood that the winch 84 is not the only possible mechanism which can be used for tightening the flexible member 110. Rather, any other suitable mechanism can be used for that purpose, such as a screw mechanism, a pneumatic or fluid operated mechanism, a motor drive, etc. Furthermore, any structure other than the tower 82 can be employed, which will move the point of force application away from the axis of rotation of the joint. Again, the hinge structure shown can, of course, be replaced by, for example, a flexible piece of plastic or some other hinge mechanism. Accordingly, the present invention is not limited to the use of a winch or a tower or hinge strictly as shown.

It should also be noted that the flexible member 110 can include or can be replaced by a resilient member, such as an elastic portion or a spring loading structure. This provides the patient with some ability to bend or flex the joint while the orthosis is attempting to extend the joint. In effect, the patient's muscles work against the force of the orthosis and providing further exercise for the muscles. The flexible member, when tensioned by the drive means, is stretched even more by the patient pulling on it in the opposite direction—resisting the extension force applied by the winch. He pulls through the range of motion. After the range of motion is obtained, the device can also be used for exercise, to lessen pain, and to retain the range of motion at any given point. The modifications to the structure shown in the drawings are obvious to one of ordinary skill, and so are shown only schematically in the drawings, as indicated by the flexible member portion 111 in FIG. 1 which is a length of the rope 110 which is to some extent stretchable or elastic as opposed to the remainder thereof which firmly transmits the extension force to the arm assemblies.

Any of the orthoses of the present invention may also include means for providing three distinct areas of application of force to the limb. In addition to the two cuff assemblies which apply force at locations as far distant as possible from the joint to increase mechanical advantage, means can be provided for applying force in the opposite direction to the area of the limb adjacent the joint. This would include, for example, a cup on the outside of the elbow or knee or straps extending around the elbow or knee. Such modification can easily be made in accordance with the teachings of the prior art, for example as shown in the Best, Brown, or Lonardo patents identified above.

From the above description of the invention, those skilled in the art will perceive improvements, changes and modifications. Such improvements, changes and modifications within the skill of the art are intended to be covered by the appended claims.

I claim:

1. An orthosis for stretching tissue around a joint of a patient between first and second relatively pivotable body portions, the joint and the first and second body portions body portions, the joint and the first and second body portions defining on one side of the joint is flexed and defining on the opposite side of the joint an outer sector which decreases in angle as the joint is extended, comprising
    a first rigid arm, and first cuff means on said first arm for releasably attaching said first arm to the first body portion;
    a second rigid arm, and second cuff means on said second arm for releasably attaching said second arm to the second body portion;
    means for pivotally connecting said first and second arms with each other intermediate said first and second cuff means; and
    actuator means connected to said first and second arms for receiving a force not generated by movement of the first or second body portions and for applying said force to said first and second arms to pivot said first and second arms relative to each other to move the joint, said actuator means including
    flexible force transmitting means connected with at least one of said arms, and
    drive means for applying force to said flexible force transmitting means to move said first and second arms relative to each other.

2. An orthosis as defined in claim 1 wherein said drive means is located in the outer sector.

3. An orthosis as defined in claim 1 wherein said flexible force transmitting means is connected with said first arm and with said second arm and with said drive means.

4. An orthosis as defined in claim 1 wherein said drive means is operable to adjust the orthosis to a plurality of different positions by pivoting said first and second arms relative to each other to move the joint while the orthosis is attached to the first and second body portions, said plurality of different positions including at least a first position in which the joint is flexed to a relatively greater degree and a second position in which the joint is extended to a relatively greater degree.

5. An orthosis as defined in claim 4 wherein said flexible force transmitting means is connected with both of said first and second arms.

6. An orthosis as defined in claim 1 including means for monitoring the force transmitted through said flexible force transmitting means to said first and second arms.

7. An orthosis as defined in claim 1 including relief means for limiting the amount of force transmitted through said flexible force transmitting means to said first and second arms.

8. An orthosis for stretching tissue around a joint of a patient between first and second relatively pivotable body portions, the joint and the first and second body portions defining on one side of the joint an inner sector which decreases in angle as the joint is flexed and defining on the opposite side of the joint an outer sector which decreases in angle as the joint is extended, comprising
    a first longitudinally extending rigid arm having inner and outer ends, said first arm including a first cuff adjacent said outer end of said first arm for releasably attaching said first arm to the first body portion;
    a second longitudinally extending rigid arm having inner and outer ends, said second arm including a second cuff adjacent said outer end of said second arm for releasably attaching said second arm to the second body portion;
    means for pivotally connecting said first and second arms with each other intermediate said first and second cuff means; and
    actuator means connected to said first and second arms for receiving a force not generated by movement of the first or second body portions and for applying said force to said first and second arms to pivot said first and second arms relative to each other to move the joint, said actuator means including
    flexible force transmitting means connected with said outer end of one of said arms,
    drive means for applying force to said flexible force transmitting means to move said first and second arms relative to each other, and
    means for applying reaction force to said inner end of said one arm.

9. An orthosis as defined in claim 8 wherein said means for applying reaction force comprises a rigid support member extending between said drive means and said means for pivotally connecting said first and second arms.

10. An orthosis as defined in claim 9 wherein said rigid support member is located in the outer sector.

11. An orthosis for stretching tissue around a joint between first and second relatively pivotable body portions, the joint and the first and second body portions defining on one side of the joint an inner sector which decreases in angle as the joint is flexed and defining on the opposite side of the joint an outer sector which decreases in angle as the joint is extended, comprising
    a first arm, and first cuff means on said first arm for releasably attaching said first arm to the first body portion;
    a second arm, and second cuff means on said second arm for releasably attaching said second arm to the second body portion;

means for pivotally connecting said first and second arms with each other at a pivot axis intermediate said first and second cuff means; and actuator means connected to said first and second arms for applying force to said first and second arms to pivot said first and second arms relative to each other to move the joint, said actuator means including a rigid support member having an inner end connected with said means for pivotally connecting said first and second arms and an outer end, flexible force transmitting means connected between said outer end of said rigid support member and said first and second arms, and means for increasing the length of said rigid support member to apply force to said flexible force transmitting means to move said first and second arms relative to each other.

12. An orthosis as defined in claim 11 wherein said rigid support member is located in the outer sector.

13. An apparatus as defined in claim 12 wherein said means for increasing the length of said rigid support member is fluid pressure operated.

14. An apparatus as defined in claim 12 wherein said means for increasing the length of said rigid support member an elongate threaded member and nut means movable relative to said threaded member.

15. An apparatus for applying force to a limb of a person on opposite sides of a joint in that limb, said apparatus comprising a first rigid member, means for connecting an outer end portion of said first rigid member with the limb of the person at a location spaced from the joint with said first rigid member extending along the limb in a first direction from the joint, a second rigid member, means for connecting an outer end portion of said second rigid member with the limb of the person at a location spaced from the joint with said second rigid member extending along the limb in a second direction from the joint, means for pivotally interconnecting inner end portions of said first and second members adjacent the joint, and actuator means for pivoting said first and second rigid members relative to each other about said inner end portions of said first and second rigid members to move the joint, said actuator means including means for simultaneously applying forces to said inner and outer end portions of said first and second rigid members urging said first and second rigid members to pivot in opposite directions relative to each other.

16. An apparatus as set forth in claim 15 wherein said means for simultaneously applying forces to the inner and outer end portions of said first and second rigid members includes means for applying first forces to the outer end portions of said first and second rigid members with the lines of action of the first forces extending at acute angles to longitudinal central axes of said first and second rigid members and means for applying second forces to inner end portions of said first and second rigid members with the lines of action of the second forces extending transversely to the lines of action of the first forces and to the longitudinal central axes of said first and second rigid members.

17. An orthosis for stretching tissue around a joint of a patient between first and second relatively pivotable body portions, the joint and the first and second body portions defining on one side of the joint an inner sector which decreases in angle as the joint is flexed and defining on the opposite side of the joint an outer sector which decreases in angle as the joint is extended, comprising a first arm, and first cuff means on said first arm for releasably attaching said first arm to the first body portion;

a second arm, and second cuff means on said second arm for releasably attaching said second arm to the second body portion;

means for pivotally connecting said first and second arms with each other intermediate said first and second cuff means; and actuator means connected to said first and second arms including:

means for receiving a force not generated by movement of the first or second body portions and for applying said force to said first and second arms to pivot said first and second arms relative to each other to move the joint, said receiving means being spaced from the joint axis and located in the outer sector at a distance from said means for pivotally connecting said first and second arms to provide a mechanical advantage, and force transmitting means intermediate said force receiving means and said first and second arms and disposed at least partially in said outer sector.

18. An orthosis for stretching tissue around a joint of a patient between first and second relatively pivotable body portions, the joint and the first and second body portions defining on one side of the joint an inner sector which decreases in angle as the joint is flexed and defining on the opposite side of the joint an outer sector which decreases in angle as the joint is extended, comprising a first arm, and a first cuff means on said first arm for releasably attaching said first arm to the first body portion;

a second arm, and second cuff means on said second arm for releasably attaching said second arm to the second body portion;

means for pivotally connecting said first and second arms with each other intermediate said first and second cuff means; and actuator means connected to said first and second arms for receiving a force not generated by movement of the first or second body portions and for applying said force to said first and second arms to pivot said first and second arms relative to each other to move the joint, said actuator means including force transmitting means connected with at least one of said arms, and drive means for placing said force transmitting means in tension to move said first and second arms relative to each other.

19. An orthosis for stretching tissue around a joint between first and second relatively pivotable body portions, the joint and the first and second body portions defining on one side of the joint an inner sector which decreases in angle as the joint is flexed and defining on the opposite side of the joint an outer sector which decreases in angle as the joint is extended, comprising a first arm, and first cuff means on said first arm for releasably attaching said first arm to the first body portion;

a second arm, and second cuff means on said second arm for releasably attaching said second arm to the second body portion;

means for pivotally connecting said first and second arms with each other intermediate said first and second cuff means; and actuator means connected to said first and second arms for applying force to said first and second arms to pivot said first and second arms relative to each other to move the joint, said actuator means including flexible force transmitting means connected with at least one of said arms, and drive means for applying force to said flexible force transmitting means to move said first and second arms relative to each other;

wherein said flexible force transmitting means is connected with said first arm and with said second arm and with said drive means; and wherein said drive means comprises manually actuatable winch means for winding said flexible force transmitting means to apply force to said first and second arms through said flexible force transmitting means.

20. An orthosis as defined in claim 19 comprising a support member interconnecting said drive means and said means for pivotally connecting said first and second arms, said support member being located in the outer sector.

21. An orthosis as defined in claim 20 wherein said drive means is located in the outer sector at a substantial distance from said means for pivotally connecting said first and second arms.

22. An orthosis for stretching tissue around a joint between first and second relatively pivotable body portions, the joint and the first and second body portions defining on one side of the joint an inner sector which decreases in angle as the joint is flexed and defining on the opposite side of the joint an outer sector which decreases in angle as the joint is extended, comprising a first arm, and first cuff means on said first arm for releasably attaching said first arm to the first body portion;

a second arm, and second cuff means on said second arm for releasably attaching said second arm to the second body portion;

means for pivotally connecting said first and second arms with each other intermediate said first and second cuff means; and actuator means connected to said first and second arms for applying force to said first and second arms to pivot said first and second arms relative to each other to move the joint, said actuator means including flexible force transmitting means connected with at least one of said arms, and drive means for applying force to said flexible force transmitting means to move said first and second arms relative to each other;

wherein said drive means is operable to adjust the orthosis to a plurality of different positions by pivoting said first and second arms relative to each other to move the joint while the orthosis is attached to the first and second body portions, said plurality of different positions including at least a first position in which the joint is flexed to a relatively greater degree and a second position in which the joint is extended to a relatively greater degree;

wherein said flexible force transmitting means is connected with both of said first and second arms; and wherein a first portion of said flexible force transmitting means and said first arm define a first included angle therebetween which increases as said orthosis is adjusted from said first position to said second position, and a second portion of said flexible force transmitting means and said second arm define a second included angle therebetween which increases as said orthosis is adjusted from said first position to said second position.

23. An orthosis as defined in claim 22 wherein said drive means comprises means for pulling on said flexible force transmitting means to shorten the distance between said drive means and the point where said flexible force transmitting means is attached to said first arm and to shorten the distance between said drive means and the point where said flexible force transmitting means is attached to said second arm to adjust the orthosis from said first position to said second position.

24. An orthosis for stretching tissue around a joint between first and second relatively pivotable body portions, the joint and the first and second body portions defining on one side of the joint an inner sector which decreases in angle as the joint is flexed and defining on the opposite side of the joint an outer sector which decreases in angle as the joint is extended, comprising a first arm, and first cuff means on said first arm for releasably attaching said first arm to the first body portion;

a second arm, and second cuff means on said second arm for releasably attaching said second arm to the second body portion;

means for pivotally connecting said first and second arms with each other intermediate said first and second cuff means; and actuator means connected to said first and second arms for applying force to said first and second arm to pivot said first and second arms relative to each other to move the joint, said actuator means including flexible force transmitting means connected with at least one of said arms, and drive means for applying force to said flexible force transmitting means to move said first and second arms relative to each other;

wherein said first arm includes guide means for said flexible force transmitting means disposed intermediate said means for pivotally connecting said first and second arms and said first cuff means, said flexible force transmitting means extending from said drive means to said guide means and thence to said first cuff means.

25. An orthosis as defined in claim 24 wherein said guide means comprises a pulley, and said flexible force transmitting means extends at least partially around said pulley.

26. An orthosis for stretching tissue around a joint between first and second relatively pivotable body portions, the joint and the first and second body portions defining on one side of the joint an inner sector which decreases in angle as the joint is flexed and defining on the opposite side of the joint an outer sector which decreases in angle as the joint is extended, comprising a first longitudinally extending arm having inner and outer ends, said first arm including a first cuff adjacent said outer end of said first arm for releasably attaching said first arm to the first body portion;

a second longitudinally extending arm having inner and outer ends, said second arm including a second cuff adjacent said outer end of said second arm for releasably attaching said second arm to the second body portion;

means for pivotally connecting said first and second arms with each other intermediate said first and second cuff means; and actuator means connected to said first and second arms for applying force to said first and second arms to pivot said first and second arms relative to each other to move the joint, said actuator means including flexible force transmitting means connected with said outer end of one of said arms, drive means for applying force to said flexible force transmitting means to move said first and second arms relative to each other, and means for applying reaction force to said inner end of said one arm;

wherein said means for applying reaction force comprises a rigid support member interconnecting said drive means and said means for pivotally connecting said first and second arms;

wherein said rigid support member is located in the outer sector; and wherein said drive means is operable to adjust the orthosis to a plurality of different positions by pivoting said first and second arms relative to each other to move the joint while the orthosis is attached to the first and second body portions, said plurality of different positions including at least a first position in which the joint is flexed to a relatively greater degree and a second position in which the joint is extended to a relatively greater degree;

said flexible force transmitting means is connected with both of said first and second arms, a first portion of said flexible force transmitting means and said first arm define a first included angle therebetween which increases as said orthosis is adjusted from said first position to said second position, and a second portion of said flexible force transmitting means and said second arm define a second included angle therebetween which increases as said orthosis is adjusted form said first position to said second position; and said drive means comprises means for pulling on said flexible force transmitting means to shorten the distance between said drive means and said first cuff means and to shorten the distance between said drive means and said second cuff means to adjust the orthosis from said first position to said second position.

27. An apparatus for applying force to a limb of a person on opposite sides of a joint, said apparatus comprising a first rigid member, means for connecting an outer end portion of the first rigid member with the limb of the person at a location spaced from the joint with the first rigid member extending along the limb in a first direction from the joint, means for connecting an outer end portion of the second rigid member with the limb of the person at a location spaced from the joint with the second rigid member extending along the limb in a second direction from the joint, means for pivotally interconnecting inner end portions of the first and second members adjacent the joint, and actuator means for pivoting the first and second rigid members relative to each other about the inner end portions of said first and second rigid members to move the joint, said actuator means including means for simultaneously applying forces to said inner and outer end portions of said first and second rigid members urging said first and second rigid members to pivot in opposite directions relative to each other, and including a third rigid member extending transversely to the first and second rigid members, said third rigid member having a first end portion connected to the inner end portions of the first and second rigid member adjacent to the joint and a second end portion spaced from the joint, said means for simultaneously applying forces to the inner and outer end portions of the first and second rigid members including first force transmitting means extending from the second end portion of the third rigid member to the outer end portion of the first rigid member and second force transmitting means extending from the second end portion of the third rigid member to the outer end portion of the second member.

28. An apparatus as set forth in claim 27 wherein said means for simultaneously applying forces to the inner and outer end portions of said first and second rigid member includes manually actuatable drive means mounted on the second end portion of the third rigid member and connected with said first and force transmitting means, said manually actuatable drive means being operable to pull said first and second force transmitting means toward the second end portion of said third rigid member.

29. An apparatus as set forth in claim 28 wherein said first and second force transmitting means are flexible and said drive means includes winch means for winding said first and second force transmitting means about an axis extending through the outer end portion of said third rigid member.

30. An apparatus for applying force to a limb of a person on opposite sides of a joint, said apparatus comprising a first rigid member, means for connecting an outer end portion of the first rigid member with the limb of the person at a location spaced from the joint with the first rigid member extending along the limb in a first direction from the joint, means for connecting an outer end portion of the second rigid member with the limb of the person at a location spaced from the joint with the second rigid member extending along the limb in a second direction from the joint, means for pivotally interconnecting inner end portions of the first and second members adjacent the joint, and actuator means for pivoting the first and second rigid members relative to each other about the inner end portions of said first and second rigid members to move the joint, said actuators means including means for simultaneously applying forces to said inner and outer end portions of said first and second rigid members urging said first and second rigid members to pivot in opposite directions relative to each other;

wherein said means for simultaneously applying forces to the inner and outer end portions of the first and second member includes first flexible force transmitting means connected with the outer end portion of said first rigid member and second flexible force transmitting means connected with the outer end portion of said second rigid member and manually actuatable winch means for winding up said first and second flexible force transmitting means.

31. An apparatus as set forth in claim 30 wherein said winch means includes drum means rotatable about an axis extending parallel to axes about which said first and second rigid members pivot relative to each other upon operation of said actuator means.

32. An apparatus for applying force to a limb of a person on opposite sides of a joint, said apparatus comprising a first rigid member, means for connecting an outer end portion of the first rigid member with the limb of the person at a location spaced from the joint with the first rigid member extending along the limb in a first direction from the joint, means for connecting an outer end portion of the second rigid member with the limb of the person at a location spaced from the joint with the second rigid member extending along the limb in a second direction from the joint, means for pivotally interconnecting inner end portions of the first and second members adjacent the joint, and actuator means for pivoting the first and second rigid members relative to each other about the inner end portions of said first and second rigid members to move the joint, said actuator means including means for simultaneously applying forces to said inner and outer end portions of said first and second rigid members urging said first and second rigid members to pivot in opposite directions relative to each other;

wherein said actuator means includes a third rigid member having a first end portion connected with the inner end portions of said first and second rigid members, means for increasing the length of said third rigid member, and means for transmitting force from a second end portion of said third rigid member to the outer end portions of said first and second rigid members as the length of said third rigid member increases.

33. An apparatus for applying force to a limb of a person on opposite sides of a joint, said apparatus comprising a first rigid member, means for connecting an outer end portion of the first rigid member with the limb of the person at a location spaced from the joint with the first rigid member extending along the limb in a first direction from the joint, means for connecting an outer end portion of the second rigid member with the limb of the person at a location spaced for the joint with the second rigid member extending along the limb in a second direction from the joint, means for pivotally interconnecting inner end portions of the first and second members adjacent the joint, and actuator means for pivoting the first and second rigid members relative to each other about the inner end portions of said first and second rigid members to move the joint, said actuator means including means for simultaneously applying forces to said inner and outer end portions of said first and second rigid members urging said first and second rigid members to pivot in opposite directions relative to each other;

wherein said first and second force transmitting means are flexible and said drive means includes winch means for winding said first and second force transmitting means about an axis extending through the outer end portion of said third rigid member; and wherein at least one of said first and second flexible force transmitting means includes an elastic portion.

34. An orthosis for stretching tissue around a joint of a patient between first and second relatively pivotable body portions, the joint and the first and second body portions defining on one side of the joint an inner sector which decreases in angle as the joint is flexed and defining on the opposite side of the joint an outer sector which decreases in angle as the joint is extended, comprising:

a first rigid arm, and first cuff means on said first arm for releasably attaching said first arm to the first body a second rigid arm, and second cuff means on said second arm for releasably attaching said second arm to the second body portion;

means for pivotally connecting said first and second arms with each other intermediate said first and second cuff means; and actuator means connected to said first and second arms for receiving a force into generated by movement of the first or second body portions and for applying said force to said first and second arms to pivot said first and second arms relative to each other to move the joint, said actuator means including first and second force transmitting members having outer end portions connected to said first and second arms, respectively, said first and second force transmitting members extending from said arms in a direction into the outer sector and having inner end portions connected to a portion of said actuator means in the outer sector at a location spaced from the joint and spaced from said means for pivotally interconnecting said first and second arms.

35. An orthosis as defined in claim 34 wherein said first and second force transmitting members are flexible.

36. An orthosis for stretching tissue around a joint of a patient between first and second relatively pivotable body portions, the joint and the first and second body portions defining on one side of the joint an inner sector which decreases in angle as the joint is flexed and defining on the opposite side of the joint an outer sector which decreases in angle as the joint is extended, comprising:

a first rigid arm, and first cuff means on said first arm for releasably attaching said first arm to the first body portion;

a second rigid arm, and second cuff means on said second arm for releasably attaching said second arm to the second body portion; and means for interconnecting said first and second arms with each other intermediate said first and second cuff means, comprising:

means for pivotally connecting said first and second arms with each other intermediate said first and second cuff means, a tower extending from said means for pivotally connecting in a direction into the outer sector, and first and second force transmitting members connected with said first and second arms, respectively, said first and second force transmitting members extending between said arms and said tower and being connected with said tower in the outer sector at a location spaced from said means for pivotally interconnecting said first and second arms.

37. An orthosis as defined in claim 36 including actuator means connected to said force transmitting members for receiving a force not generated by movement of the first or second body portions and for applying said force to said force transmitting members to pivot said first and second arms relative to each other to move the joint.

* * * * *

UNITED STATES PATENT AND TRADEMARK OFFICE
CERTIFICATE OF CORRECTION

PATENT NO. : 5,167,612

DATED : December 1, 1992

INVENTOR(S) : Peter M. Bonutti

It is certified that error appears in the above-identified patent and that said Letters Patent is hereby corrected as shown below:

Column 11, Line 26, Claim 1, Delete "body portions, the joint and the first and sec-".

Column 11, Line 27, Claim 1, Delete "ond body portions".

Column 11, Line 27, Claim 1, After "joint" insert --an inner sector which decreases in angle as the joint--.

Column 16, Line 40, Claim 24, Change "arm" to --arms--.

Column 17, Line 48, Claim 26, Change "form" to --from--.

Column 18, Line 55, Claim 30, Change "actuators" to --actuator--.

Column 18, Line 63, Claim 30, Change "member" to --members--.

Column 20, Line 7, Claim 34, After "body" insert --portion;--.

Column 20, Line 15, Claim 34, Change "into" to --not--.

Signed and Sealed this

Seventh Day of December, 1993

Attest:

BRUCE LEHMAN

*Attesting Officer*   *Commissioner of Patents and Trademarks*